(12) United States Patent
Elton et al.

(10) Patent No.: US 7,742,168 B2
(45) Date of Patent: Jun. 22, 2010

(54) MEASURING A SURFACE CHARACTERISTIC

(75) Inventors: Nick Elton, St. Austell (GB); John Day, Bristol (GB)

(73) Assignee: Surfoptic Limited, Cornwall (GB)

( * ) Notice: Subject to any disclaimer, the term of this patent is extended or adjusted under 35 U.S.C. 154(b) by 580 days.

(21) Appl. No.: 10/554,779

(22) PCT Filed: Apr. 15, 2004

(86) PCT No.: PCT/GB2004/001634

§ 371 (c)(1), (2), (4) Date: Jan. 9, 2007

(87) PCT Pub. No.: WO2004/097383

PCT Pub. Date: Nov. 11, 2004

(65) Prior Publication Data

US 2007/0153285 A1 Jul. 5, 2007

(30) Foreign Application Priority Data

Apr. 29, 2003 (GB) .................................. 0309690.6

(51) Int. Cl.
*G01J 4/00* (2006.01)
*G01N 21/00* (2006.01)

(52) U.S. Cl. .................................... 356/369; 356/237.2

(58) Field of Classification Search .............. 356/237.2, 356/364, 369

See application file for complete search history.

(56) References Cited

U.S. PATENT DOCUMENTS

| 3,490,827 | A | 1/1970 | Ligten et al. |
| 3,922,093 | A | 11/1975 | Dandliker et al. |
| 4,210,401 | A | 7/1980 | Batten |
| 6,177,984 | B1 | 1/2001 | Jacques |
| 6,504,617 | B2 | 1/2003 | Komulainen et al. |
| 2001/0013935 | A1 | 8/2001 | Watanabe et al. |
| 2002/0171826 | A1 | 11/2002 | Wiles et al. |

FOREIGN PATENT DOCUMENTS

| GB | 2277148 A | 10/1994 |
| GB | 2277148 A * | 10/1994 |

OTHER PUBLICATIONS

International Search Report with Written Opinion of the International Searching Authority dated Jul. 30, 2004 for corresponding International Application No. PCT/GB2004/001634, filed Apr. 15, 2004, 9 pgs.

* cited by examiner

*Primary Examiner*—Roy Punnoose
(74) *Attorney, Agent, or Firm*—Sturm & Fix LLP

(57) ABSTRACT

At least one surface characteristic of a sample, e.g. gloss, refractive index, micro-roughness, macroroughness, colour shift, is determined by illuminating a surface of the sample with a collimated beam of light at an angle to the plane of the surface and using an imaging detector to record an intensity and angular distribution image of the light from the beam reflected from the surface.

33 Claims, 7 Drawing Sheets

MEASURING A SURFACE CHARACTERISTIC

CROSS-REFERENCE TO RELATED APPLICATION(S)

The present application is the National Stage of International Application No. PCT/GB2004/001634, filed Apr. 15, 2004, which claims the benefit under 35 U.S.C. §119 of United Kingdom Application No. 0309690.6, filed Apr. 29, 2003, incorporated herein by reference in their entirety.

SUMMARY OF THE INVENTION

The present invention concerns a method for measuring a surface characteristic of a sample, and apparatus for carrying out the method.

There are many applications in industry where it is essential to accurately determine a variety of optical surface characteristics, one such area being that of paper manufacturing. To regulate paper manufacture, the paper must be assessed to determine its surface properties, which usefully include the gloss, surface refractive index and the roughness.

Conventionally, the measurement of surface characteristics has been achieved by the use of a goniometer. A goniophotometer capable of measuring the angular gloss distribution of a sample (Gate & Leaity, 1991; Gate & Parsons, 1983) is shown schematically in FIG. 1. Here the sample under investigation is mounted on a vacuum table and is illuminated by a fixed polarised He—Ne laser. The detector consists of a pair of in-line pinholes to define the acceptance angle of the detector, mounted in front of an integrating sphere which carries a silicon photodiode to monitor the reflected light signal. Both the sample and the detector are mounted on a mechanical goniometer and may be rotated to vary the incidence and detection angles. The plane of polarisation of the incident light can be rotated manually to be either in the incident plane or perpendicular to it by means of a half-wave plate which rotates about the axis of the incident beam. The use of an integrating sphere ensures that the detected signal is depolarised by repeated reflections so that the measured signal is independent of any polarisation dependency of the detector. In normal use, the sample is held fixed while the detector scans a range of angles either side of the specular angle (i.e. where the angle of incidence equals the angle of reflection). Reflected intensity is greatest at the specular angle but falls off rapidly on each side, giving a roughly bell-shaped distribution. As will be discussed later, the width of the distribution is related to surface macro-roughness, i.e. the roughness on a scale greater than the wavelength of the light. By rotating the plane of polarisation of the incident light and comparing the reflected intensities, the surface refractive index may be calculated. By further comparing intensities at two angles of incidence, the micro-roughness (or surface roughness on a scale less than the wavelength of the light) can be inferred.

In use the goniometer must scan through a range of angles at a first polarisation, and then scan through the same range of angles at a second orthogonal polarisation. This makes the goniometer extremely time-consuming to use and also introduces the risk of systematic errors if the two scans are not perfectly aligned.

It is an object of the present invention to provide a method and apparatus for measuring surface characteristics of a sample more efficiently and with less chance of alignment errors. This object is achieved by obtaining all the necessary optical information in a single measurement, with no relative movement of the sample and detection apparatus.

In accordance with a first aspect of the present invention there is provided a method for determining a characteristic of a sample as set out in the accompanying claims.

In accordance with a second aspect of the present invention there is provided an apparatus for determining a surface characteristic of a sample as set out in the accompanying claims.

The invention will now be described by way of example with reference to the following figures, in which:

DETAILED DESCRIPTION

Figure 1:
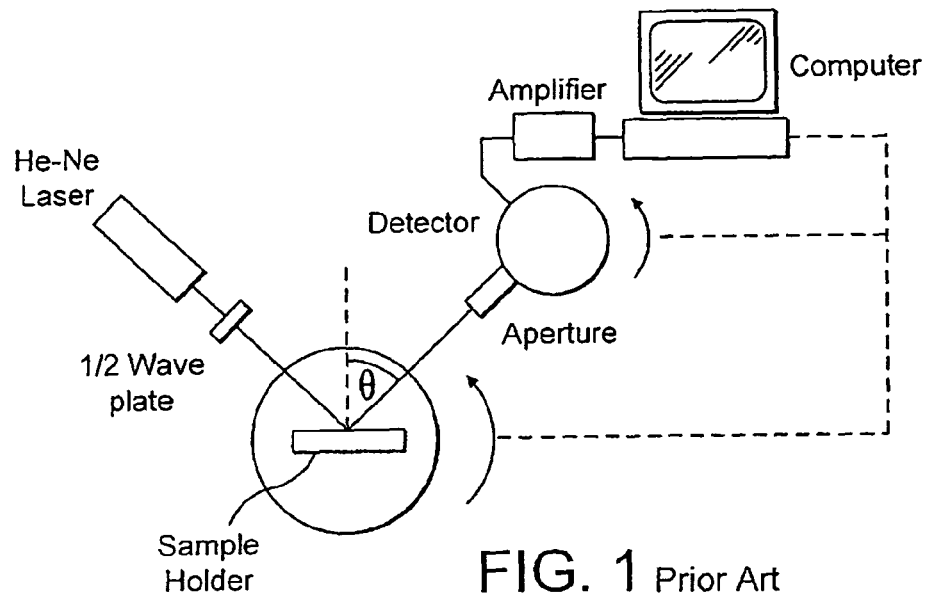
FIG. 1 shows a known arrangement for determining surface characteristics.

Before describing embodiments of the invention in detail, it is necessary to outline some of the background theory to explain how the surface characteristics of interest are derived. In particular, four such characteristics will be discussed: surface refractive index, gloss, macro-roughness and micro-roughness.

Surface Refractive Index (n):

This is a very sensitive measure of surface composition. With some prior knowledge of the material, it can give important insights into changes and properties at the surface. For example, in coated paper it can be related to particle packing and surface porosity, or in printed surfaces to the ratio of resin/ink pigment at the surface.

The reflectance of light from a perfectly smooth, homogeneous, isotropic and non-absorbing substrate is described by the Fresnel equations for S and P polarised light:

$$Rs0 = \frac{\sin^2(\theta_i - \theta')}{\sin^2(\theta_i - \theta')} \tag{1}$$

$$Rp0 = \frac{\tan^2(\theta_i - \theta')}{\tan^2(\theta_i + \theta')} \quad (2)$$

Where $$\theta' = \sin^{-1}\left(\frac{\sin\theta_i}{n}\right) \quad (3)$$

The angle $\theta_i$ is the angle of incidence and n is the refractive index of the reflecting medium. Transmission coefficients are given by $$Ts0 = 1 - Rs0 \text{ and } Tp0 = 1 - Rp0 \quad (4)$$

Thus light with an incident intensity $I_0$ has reflected intensity $R = I_0 R_0$. By measuring the ratio $Rp_0/Rs_0$, one can deduce the refractive index of the reflecting substrate. By using (1), (2) and (3), one obtains $$n = \sin\theta_i \left[1 + \left(\frac{1-\rho}{1+\rho}\right)^2 \tan^2\theta_i\right]^{1/2} \quad (5)$$

where $$\rho = \sqrt{Rp_0/Rs_0} \quad (6)$$

Therefore it can be seen that in order to determine the surface refractive index, it is necessary to use both S and P polarised light and compare their reflected intensities.

Macro-roughness:

This is roughness on a scale>wavelength of light, and may affect the gloss of the surface depending on the gloss measurement geometry. In the example of coated paper, the macro-roughness is usually dependent on the substrate of the sample, e.g. paper fibre. The macro-roughness is defined here by a facet model, which treats the surface as being made up of a distribution of facets, each of which is assumed to be perfectly smooth, homogeneous, isotropic and non-absorbing and therefore reflects light specularly according to the laws of geometrical optics, e.g. Fresnel's equations and Snell's Law. The distribution in inclination of facets to the surface normal gives rise to an angular distribution of the reflected light.

If the number distribution of facets is described by some function $F(\theta_f)$, where $\theta_f$ is the inclination of the facet from the surface normal, then the intensity reflected in the plane of incidence at some angle $\theta$ is described by $$Rs(\theta) = F(\theta - \theta_i) Rs0 \quad (7)$$

and similarly for Rp, where $\theta_f = \theta - \theta_i$. Normalisation is such that $$\int (Rs + Ts) d\theta = 1 \quad (8)$$

which implies $$\int F(\theta) = 1 \quad (9)$$

A Gaussian distribution is a well-studied form for $F(\theta_f)$, and one that works well for many surfaces:

$$F(\theta_f) = \frac{1}{\sum \sqrt{2\pi}} \exp\left(\frac{\tan^2\theta_f}{2\Sigma^2}\right) \quad (10)$$

Where it is assumed that the average slope is zero. The parameter $\Sigma$ is the half-width (at 60% full height), or, as is more commonly known, the standard deviation of the distribution (of surface slopes), and will be termed the macro-roughness. The Gaussian distribution will not give a good description of the surface if it contains bumps and pits introducing facets with extreme values of surface slope.

The above theory relates to reflection from a one dimensional surface. In practice of course, real surfaces are two dimensional and the reflection and scattering takes place in three dimensions. A given facet may be described by two angles, $\theta_f$ and $\phi_f$, being the inclination of the facet normal to the mean surface normal in the plane of reflection and orthogonal to the plane of reflection respectively. The observed angular distribution of light from a facet surface is governed by the facet distribution (eqn. (10)) and the angle of incidence $\theta_i$ according to the laws of geometrical optics.

Micro-roughness:

This is roughness on a scale≦wavelength of light and strongly affects the gloss of the surface. In paper coating, it is due to mineral particles, and in ink due largely to organic ink pigments. Because both macro and micro-roughness affect gloss, it is important to differentiate between them. They are both important for other material properties, for example the printability of a substrate.

The determination of micro-roughness here uses the analysis of Beckmann and Spizzichino (1963) for scattering from rough surfaces which gives a general solution valid for a wide range of roughness under the Kirchoff approximation.

The most important case of a random rough surface is the Gaussian distribution of surface heights z, defined such that the mean height $\langle z \rangle = 0$ and the distribution of z is given by $$w(z) = \frac{1}{\sigma\sqrt{2\pi}} \exp-\left(\frac{z^2}{2\sigma^2}\right) \quad (11)$$

where $\sigma$ is the standard deviation (and is also coincidentally equal to the rms value of surface roughness). The surface is described also by an autocorrelation function, which provides information about the density of surface irregularities:

$$C(\tau) = e^{-\tau^2/T^2} \quad (12)$$

where $\tau$ is the distance between two points and T the correlation distance, the separation for which $C(\tau)$ drops to the value 1/e.

The general (1-D) solution for the scattered intensity is $$M(\theta_i, \theta) = e^{-g}\left(\left(\frac{\sin v_x L}{v_x L}\right)^2 + \frac{\pi^{1/2} F^2 T}{2L} \sum_{m=1}^{\infty} \frac{g^m}{m! m^{1/2}} e^{-v_x^2 T^2/4m}\right) \quad (13)$$

Note $M(\theta_i, \theta) = \langle \rho\rho^* \rangle$ in Beckmann's notation, which gives the mean intensity scattered at an angle $\theta$ from the surface where the angle of incidence was $\theta_i$ and where $$v_x = \frac{2\pi}{\lambda}(\sin\theta_i - \sin\theta) \qquad (14)$$

$$F = \sec\theta_0 \left[ \frac{1 + \cos(\theta_i + \theta)}{\cos\theta_i + \cos\theta} \right] \qquad (15)$$

$$g = \left[ \frac{2\pi\sigma}{\lambda}(\cos\theta_i + \cos\theta) \right]^2 \qquad (16)$$

L is the length of the surface being examined. The principal limit on the realm of validity of the above equation is that the radius of curvature of the surface roughness features is large compared with the wavelength of light, expressed formally as $$4\pi r_c \cos\alpha \gg \lambda \qquad (17)$$

where $r_c$ is the radius of curvature and $\alpha$ the local angle of incidence. In addition it is required that L>>T and L>>$\lambda$.

As a general result, the reflectance into the specular direction is modified by a factor (Beckmann and Spizzichino 1963), giving:

$$M(\theta_i, \theta_l) = \exp{-(4\pi\sigma\cos\theta_l/\lambda)^2} = R/R_0 \qquad (18)$$

Where $\theta_i$ is the angle of incidence, $\lambda$ is the wavelength of the incident light, $\sigma$ is the micro-roughness parameter and $R_0$ is the specular reflection from an optically smooth surface of the same refractive index at the given angle of incidence.

The Beckmann model relates to a perfectly conducting rough plane, however Gate (1973) and Hensler (1992) found that the model as applied to specular reflection of dielectrics appeared valid and gave useful insights into surface micro-roughness, yielding fair correlation with roughness measured by other techniques.

Looking at eqn. (18), it can be seen that there are therefore several ways of determining micro-roughness. For example, measurements of the reflected intensity can be taken for more than one angle of incidence using the same wavelength. Alternatively, measurements of the reflected intensity can be taken for different wavelengths at the same angle of incidence.

Separating Micro- and Macro-roughness:

It has been seen that macro-roughness produces a bell-shaped intensity distribution centred on the specular angle. If micro-roughness is now also considered, it has been found that it has the effect of reducing the overall reflectance of the surface leading to a decrease in the measured intensity. It also shifts the centroid of the distribution toward higher angles, away from the specular angle. However, the width of the reflection image is not greatly affected by slight-moderate micro-roughness. For typical coated papers, experimentation has shown that $\sigma$ is commonly in the range 0.1 to 0.3 μm, while $\Sigma$ is commonly in the range 1°-3°. The differences between papers are likely to be such that at this level the width of the reflected image can reasonably be taken as a first approximation to the macro-roughness. Furthermore, the area (reflectance) under the reflected image is related almost linearly to the micro-roughness $\sigma$. This permits a further method for the determination of micro-roughness, by measuring the total reflectance or area ($A_{obs}$) under the reflection image and comparing it to a calculated total reflectance or area ($A_{calc}$) under the image produced by reflection from a smooth standard surface of known refractive index, such as highly polished glass. The ratio of $A_{calc}/A_{obs}$ can then be related to $\sigma$, e.g. by using eqn. (18). This technique will be further explained later.

Gloss:

The gloss of a surface may be defined in a number of ways (e.g. Tappi T480, DIN 54502 standards). Effectively it is a measure of the reflectance of a surface relative to some standard, but the measurement must also be defined in terms of wavelength measurement geometry, and in particular in terms of the acceptance angle of the detector. A general definition for gloss may be given (as a percentage) by $$G = 100 \frac{\iint_{\theta,\phi} R(\theta,\phi)}{R_0} \qquad (19)$$

where the integral is of reflectance over some particular solid angle. Note that R=0.5 (Rp+Rs), while $R_0$ is the reflectance of a perfectly smooth standard material of given refractive index.

To determine all of the surface refractive index, gloss, macro-roughness and micro-roughness parameters with one instrument in one static measurement step, it is necessary to provide an instrument that can supply illuminating beams of collimated light of S and P polarisation at the same wavelength and angle of incidence, and a further beam of either polarisation at either a different wavelength or a different angle of incidence, together with a detector capable of angularly resolved intensity measurement.

Figure 2:
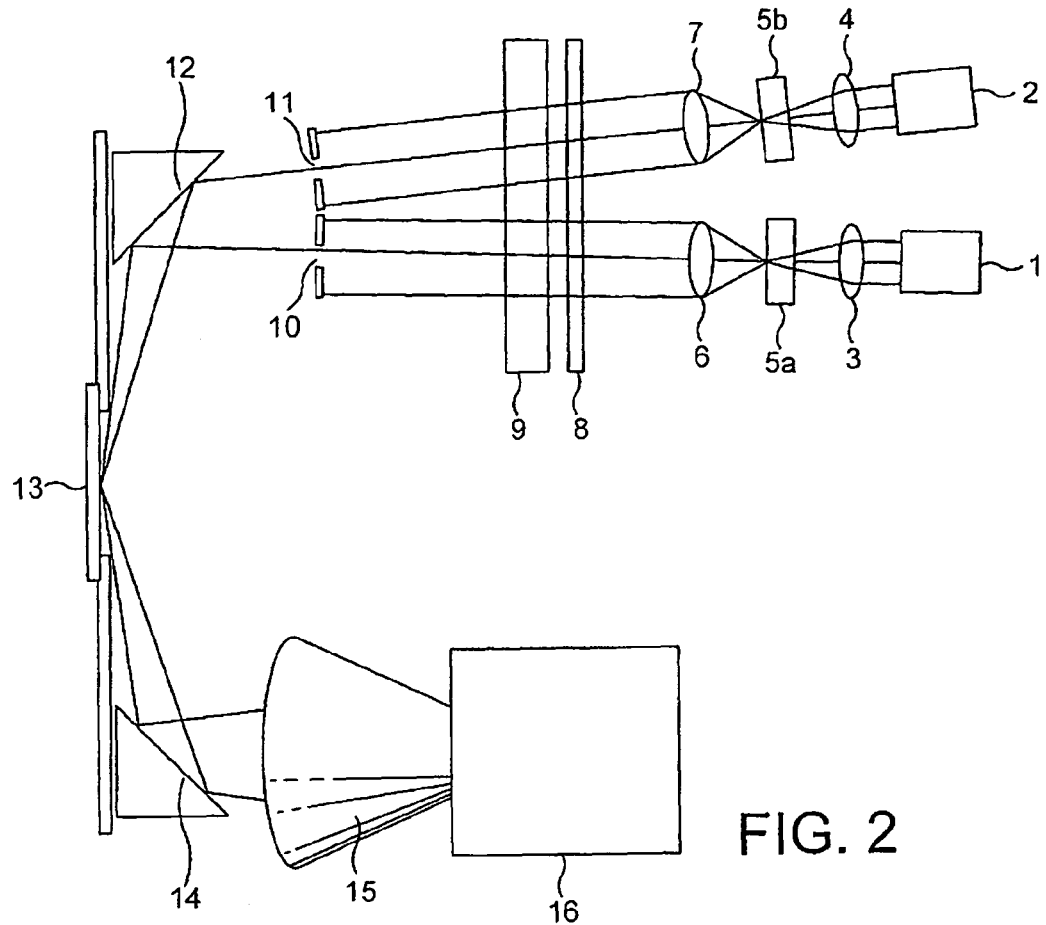
FIG. 2 shows a plan view of a first embodiment of the present invention.

FIG. 2 shows a schematic representation of a first embodiment of apparatus according to the invention. Illuminating light is produced by two lasers 1 and 2, both producing monochromatic light of wavelength 635 nm. The lasers are positioned so that the beams produced are non-parallel, being inclined at about 2°, so that eventually they illuminate the sample at different angles of incidence. The light from the lasers then pass through a "phase modulating beam expander" comprising first lenses 3, 4, spinning diffusers 5a, 5b and second lenses 6, 7. The phase modulating beam expander produces a collimated beam of light wherein the phase is modulated, so that by collecting an image of the scattered laser light over a suitable period of time, the so-called "speckle" effects in the scattered image arc reduced by time averaging. First lenses 3, 4 focus the laser light onto the surface of the spinning diffusers 5a, 5b. The diffusers comprise a layer of material such as glass or translucent plastic which is mounted to rotate at around 6200 rpm. The light passes through the diffuser and is collected by second lenses 6, 7 which are arranged to produce an image of the spot on the diffusers at infinity, i.e. the surface of the diffuser is positioned at the focal point of each lens.

The phase modulated light is then passed through a sheet polariser 8 to ensure plane polarisation in a fixed direction such that the plane of polarisation is perpendicular to the sample surface, i.e. P-polarisation. The plane polarised light then passes through a switchable polarising means, in this case a liquid crystal variable retarder 9. By applying a suitable AC voltage signal to the liquid crystal retarder, the plane of polarisation may be made to switch through 90° so that the plane of polarisation is parallel to the sample surface, i.e. S-polarisation.

The collimated light then passes through apertures 10, 11 whose diameters define a particular area of illumination on the sample. The light is reflected by a fixed plane mirror 12 such that the first beam is incident onto the surface of sample 13 at an angle of around 75° to the surface normal and the second beam is incident at an angle of around 73°. Light scattered from the sample surface within approximately ±10° is collected by a second fixed plane mirror 14 and directed onto a lens assembly 15. An imaging detector 16 is placed at the back focal point of the lens assembly such that the angle of the incoming light with respect to the optical axis is mapped to a given position on the detector.

The imaging detector 16 is for example a charge coupled device (CCD) or complementary metal oxide semiconductor (CMOS) camera, which can record an intensity angular distribution image of the scattered light, such that the intensity in a given image pixel can be related to the intensity scattered by surface facets at a given $(\theta, \phi)$ orientation. Using a static imaging detector is more efficient than using a goniometer which has a small acceptance angle and must be moved round to obtain various angular intensity measurements. The exposure time of the image of scattered light must be sufficiently long to ensure that speckle effects are substantially removed by time averaging.

In use, the reflectometer is operated as follows. Firstly, the first laser source 1 is used to produce a collimated beam, which is passed through phase modulating beam expander 3, 5a, 6. The phase modulated light is then polarised by the sheet polariser 8 to confer P-polarisation. The polarised light illuminates the surface of sample 13 at an angle of 75°. The scattered light forms an image (a) which is measured at the detector 16. Secondly, using the same laser source, the liquid crystal retarder is switched to change the plane of polarisation to produce S-polarised light. The scattered light then forms image (b) which is measured at detector 16. Thirdly, the laser source 1 is turned off, and the second laser 2 is used instead. The light is passed through phase modulating beam expander 4, 5b, 7. The phase modulated light may be polarised with either P or S polarisation, it is not important which is used. This beam illuminates the sample surface at an angle of 73°, and the scattered light forms an image (c) which is measured at detector 16.

The ratio of image intensity in images (a) and (b) gives Rp/Rs which is used with equations (5) and (6) to calculate the refractive index. In general the incident intensities of the various lasers are not the same, but the relative intensities are measured and used to adjust the value of Rp/Rs accordingly. When calculating the refractive index, the angle of incidence used should not equal the Brewster angle.

The intensity in images (a) and (b) may be integrated over a given solid angular range and used with equation (19) to calculate the gloss according to any definition so long as the acceptance angle does not exceed ±10°.

The intensity distribution through the centre of the reflection image in the $\Theta$ and $\phi$ directions is calculated by averaging a number of tracks and the half width half maximum (HWHM) obtained for the $\Theta$ direction by calculating the standard deviation of intensity about the centroid. The complete observed angular distribution of scattered light may be transformed into a distribution of facet angles for graphical display or calculation of other statistics by knowledge of the system geometry and geometrical optics. This procedure gives the macro-roughness $\Sigma$ as defined by eqn. (10).

With this apparatus, the micro-roughness can be determined by two methods:

i) Taking the ratio of intensity in images (b) and (c). If measurements of intensity at the specular angle are made with angles of incidence $\theta_0$ and $\theta_0 + \delta$ then we have $$Rs = F(\theta - \theta_0) M(\theta, \theta) Rs0 \tag{20}$$

$$Rs' = F(\theta + \delta - \theta_0 - \delta) M(\theta + \delta, \theta + \delta) Rs0(\theta_0 + \delta) \tag{21}$$

Dividing (20) and (21), the factor $F(\theta_f)$ cancels. From a knowledge of the refractive index (measured previously), the equation can be solved for $\sigma$ by using (18).

In practice, measuring at the specular angle alone is not particularly useful owing to the noise in the imaging detector. Either an area must be integrated, or repeat measurements taken (or both).

or ii) using incident intensity. The half width $\Sigma$ and the centroid of the reflection image are obtained either by direct calculation or fitting a Gaussian to the observed 2D image. This effectively defines $F(\theta_f)$. The observed area under the image $A_{obs}$ (i.e. the total reflectance) is also measured. The incident intensity $I_0$ is also measured, using a suitable calibration method. This may be done by measuring the reflectance R of a highly polished glass standard of known refractive index and assumed to have negligible roughness. The Fresnel equations (1)-(3) are used to calculate the incident intensity as $Rp = Ip_0 Rp_0$ etc. $F(\theta_f) Rs(\theta) I_0$ may then be numerically integrated to obtain a calculated area under the image $A_{calc}$. This calculation requires knowledge of the refractive index n. Finally the ratio $A_{calc}/A_{obs}$ can be related to $\sigma$, e.g. using equation (18). This calculation yields two values of the micro-roughness $\sigma$ corresponding to S and P polarised light. The average is reported as the micro-roughness by Total Integrated Reflectance (TIR). It should be noted that there are a number of assumptions implicit in this method. For example, it is assumed that there is no absorption, no diffuse/multiple scattering, no transmission losses due to inhomogeneity of the medium, and that the form of $F(\theta_f)$ is Gaussian. It is also likely that there will be losses due to light being scattered outside the range of the detector. For these reasons the preferred method for determining micro-roughness is by using two angles, as outlined in (i) above.

Figure 3:
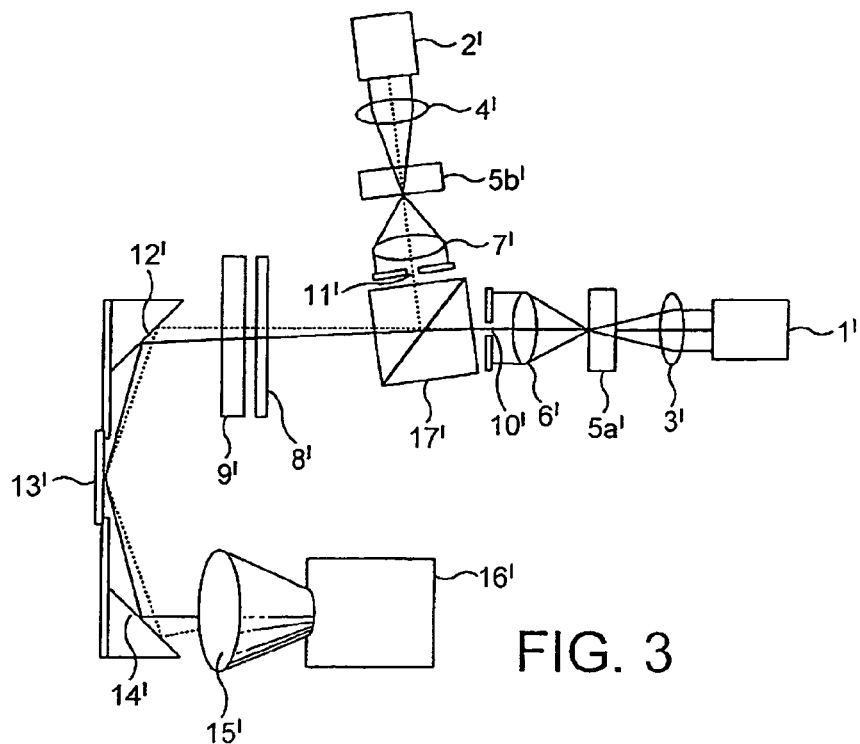
FIG. 3 shows a plan view of a second embodiment of the present invention.

FIG. 3 shows an alternative embodiment of the invention which also uses two different illumination angles to determine micro-roughness. With this arrangement there are two laser light sources 1', 2' producing laser light of the same wavelength, the lasers arranged to produce beams which are both non-parallel and non-orthogonal. Each laser is associated with its own phase modulating beam expander 3', 5a', 6' and 4', 5b', 7' through which the light passes. The light then passes through apertures 10', 11' whose areas define a particular area of illumination on the sample. The angular divergence of the beams necessary for illuminating the sample at two different illumination angles is created by use of an inclined beam-splitter 17', through which both beams pass. The diverged beams then pass through a sheet polariser 8' and liquid crystal retarder 9' as in the previous embodiment. The guiding mirrors 12', 14', sample 13', lens assembly 15' and detector 16' are all arranged in the same manner as in the previous embodiment. In this embodiment the inclined beam-splitter can again produce diverging beams so that the light from laser 1' illuminates sample 13' at an angle of about 75°, while the light from laser 2' illuminates the sample 13' at about 73°. The surface characteristics can then be determined in the same manner as for the previous embodiment.

Figure 4:
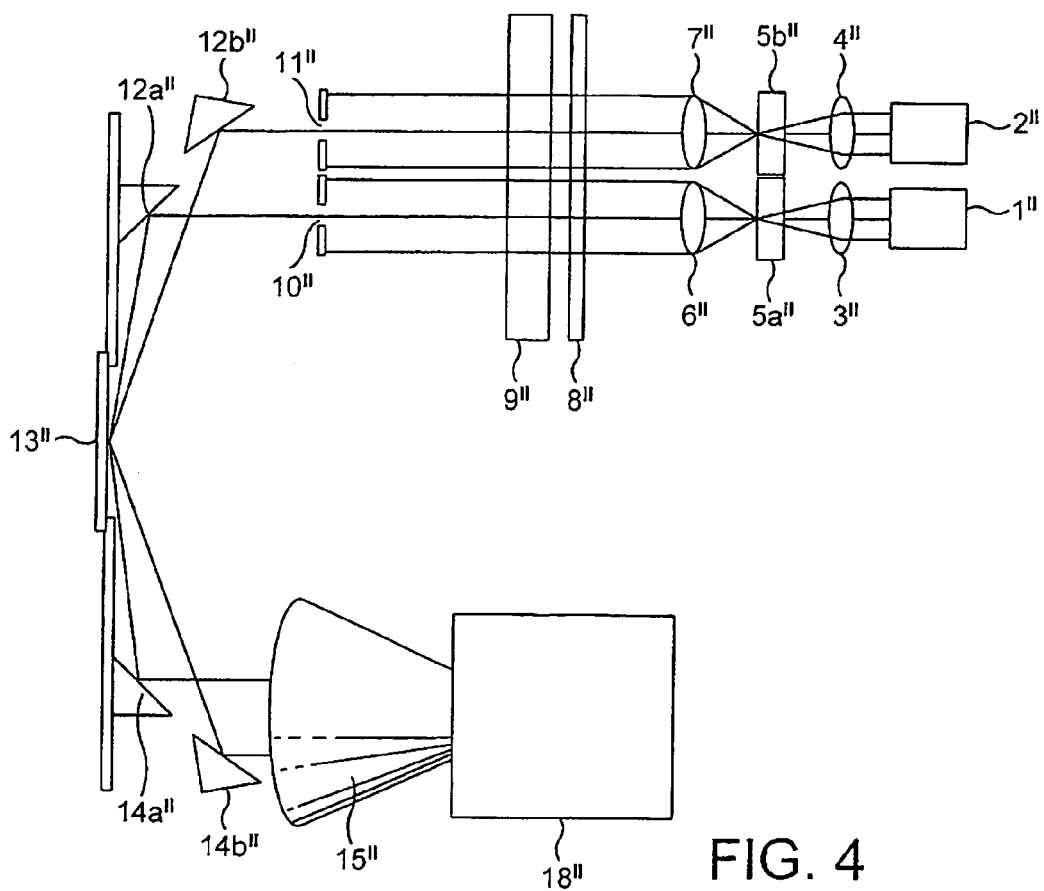
FIG. 4 shows a plan view of a third embodiment of the present invention.

FIG. 4 shows a yet further embodiment which uses two different illumination angles, and is particularly suitable for measurement of high-gloss samples. Here, two lasers 1", 2" are arranged to produce light of the same wavelength along a substantially parallel optical axis. The beams pass through their associated phase modulating beam expanders 3", 5a", 6" and 4", 5b", 6", sheet polariser 8" and liquid crystal retarder 9" as before. The beams then pass through apertures 10", 11" before reaching separate plane mirrors 12a", 12b". The mirrors are inclined so that the light from laser 1" illuminates sample 13" at 75° and the light from laser 2" illuminates the sample 13" at 73°. Complementary plane mirrors 14a", 14b" guide the resulting scattered beams into the lens assembly 15", detector 16".

Figure 5:
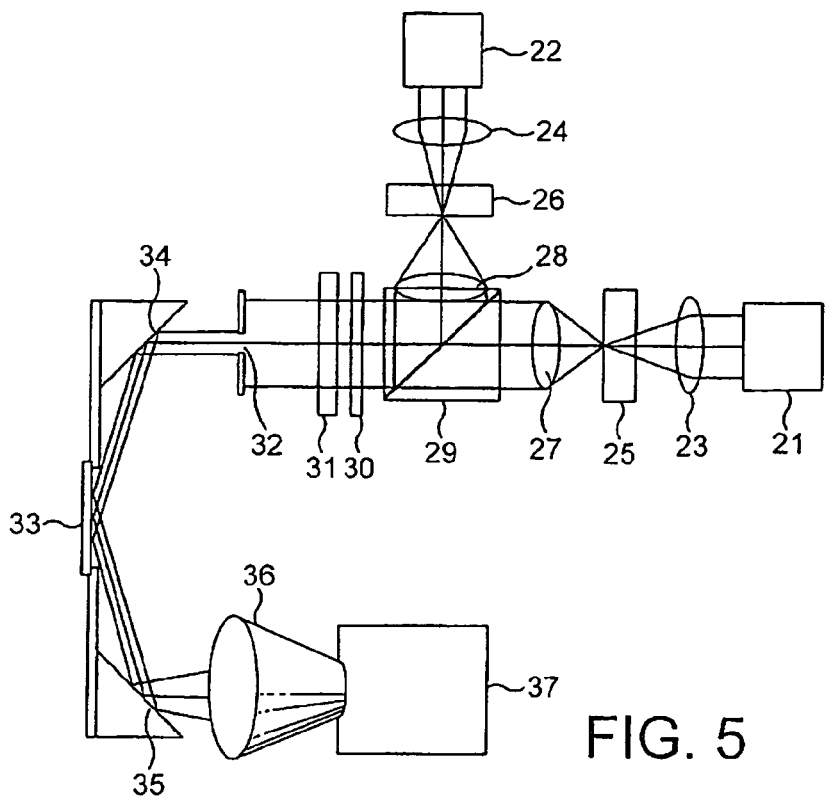
FIG. 5 shows a plan view of a fourth embodiment of the present invention.

As an alternative to using two beams of the same wavelength but different illuminating angles, it is possible to utilise two beams arranged at the same illuminating angle but with different wavelengths. Such an arrangement is shown in FIG. 5. In this embodiment, two laser sources 21, 22 are used to provide illumination. Source 21 produces light of wavelength 635 or 645 nm for example, while source 22 produces light of 670 or 690 nm. Sources 21 and 22 are arranged to produce beams with generally orthogonal optical axes. Phase modulating beam expanders 23, 25, 27 and 24, 26, 28 are again used to substantially phase modulate each beam. The beams then enter beam-splitter 29, so that the beam from source 21 is transmitted through, while the beam from source 22 is reflected, so that the beams leaving the beam-splitter are coincident. The beams are then polarised by sheet polariser 30 as well as passing through liquid crystal retarder 31 which is switchable to change the plane of polarisation by 90°. The polarised beams then pass through aperture 32, the diameter of which defines the area of illumination of the sample 33. The beams are guided onto the surface of sample 33 at the same angle of incidence of around 75° by plane mirror 34. A second plane mirror 35 guides the scattered light into lens assembly 36 and imaging detector 37.

In use, this arrangement of reflectometer is operated as follows. Firstly, the first laser source 21 is used to produce a collimated beam which is passed through phase modulating beam expander 23, 25, 27. This beam is polarised by the sheet polariser 30 to confer P-polarisation. The polarised light illuminates the surface of sample 33 at an angle of 75°. The scattered light forms an image (a) which is measured at the detector 37. Secondly, using the same laser source, the liquid crystal retarder is switched to change the plane of polarisation to produce S-polarised light. The scattered light then forms image (b) which is measured at detector 37. Thirdly, the laser source 21 is turned off, and the second laser 22, which has a different wavelength, is used instead. This produces a collimated beam which is phase modulated by phase modulating beam expander 24, 26, 28. The beam may be polarised with either P or S polarisation depending on the switching state of the liquid crystal retarder. It is not important which polarisation direction is used. The beam illuminates the sample surface at an angle of 75°, and the scattered light forms an image (c) which is measured, time-averaged, at detector 37.

The refractive index, gloss and macro-roughness are then determined in exactly the same manner as for the first embodiment, as images (a) and (b) correspond in both cases.

The micro-roughness may be determined in two ways:
i) Using incident intensity. This method is the same as that used for the first embodiment.
ii) Taking the ratio of intensity in images (b) and (c). Since the factor $F(\theta_f)$ is independent of wavelength, the factor cancels when equations (20) and (21) are divided. From a knowledge of the ratio of incident intensity corresponding to images (b) and (c), such as may be determined by measuring a smooth standard material of known refractive index, or directly, by measuring beam intensity using a photodiode, the equation can be solved for σ by using (18).

The arrangement shown in FIG. 5 requires that the liquid crystal retarder 31 is optimised for the wavelengths of both lasers 21 and 22. An alternative arrangement is to place the liquid crystal retarder 31 and sheet polariser 30 after lens 27 and before the beam-splitter 29. In this arrangement, the light from laser 22 would be plane polarised either parallel or perpendicular with respect to the sample surface by a suitable fixed polariser located between lens 28 and beam-splitter 29.

Figure 6:
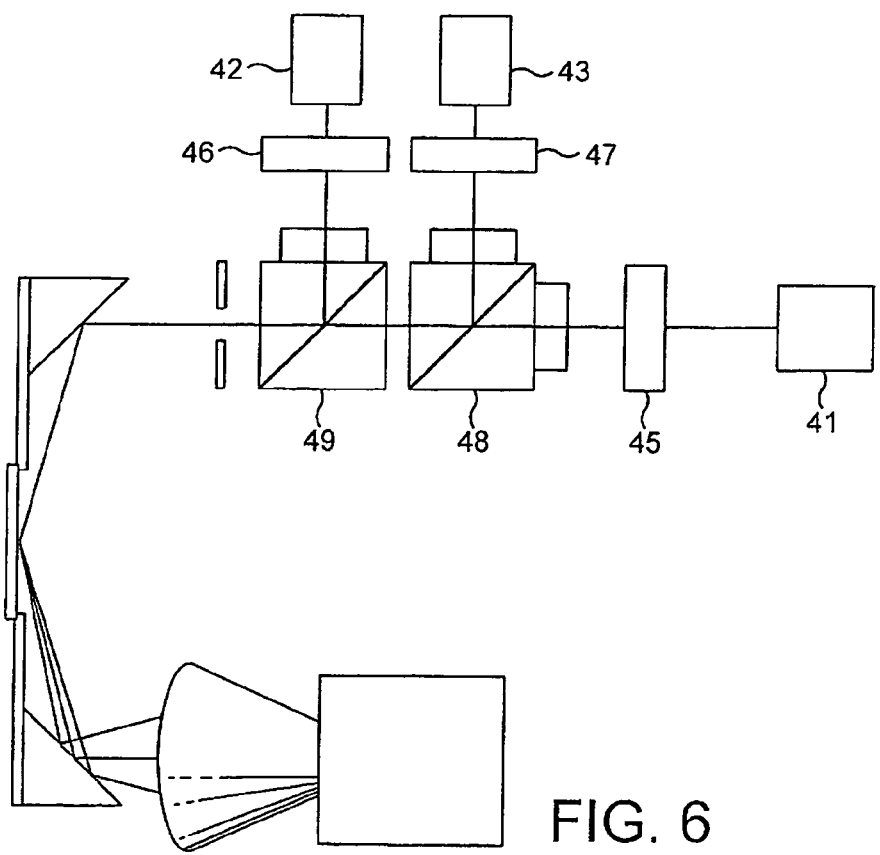
FIG. 6 shows a plan view of a fifth embodiment of the present invention.

An alternative arrangement using light of two wavelengths is shown in FIG. 6. Here, three lasers are used. Laser 41 produces a beam of collimated light of wavelength 635 nm. Laser 42 also produces a beam of collimated light of wavelength 635 nm, but with an optical axis generally orthogonal to the beam from laser 41. Laser 43 meanwhile produces a beam of collimated light of wavelength 670 nm, with an optical axis generally parallel to the beam from laser 42. Each beam passes through a respective phase modulating beam expander 45, 46. The beams from lasers 41 and 43 enter beam-splitter 48, so that the beam from laser 41 is transmitted through the beam-splitter, while the beam from laser 43 is reflected by it, so that the outgoing beams are coincident The phase modulated beams from all three lasers enter a polarising beam-splitter 49. The beams from lasers 41 and 43 are transmitted through the polarising beam-splitter, so that they obtain P-polarisation. The beam from laser 42 is reflected by polarising beam-splitter, so that it obtains S-polarisation, and leaves the beam-splitter coincident with the beams from lasers 41 and 43. All three beams are guided onto the sample at the same angle of incidence in the same manner as in the previous embodiment. With this arrangement, the lasers are turned on sequentially, so that the images produced are obtained independently. Light from laser 41 produces image (a), light from laser 42 produces image (b), and light from laser 43 produces image (c). The surface characteristics of the sample can then be determined as for the previous embodiment.

Figure 7:
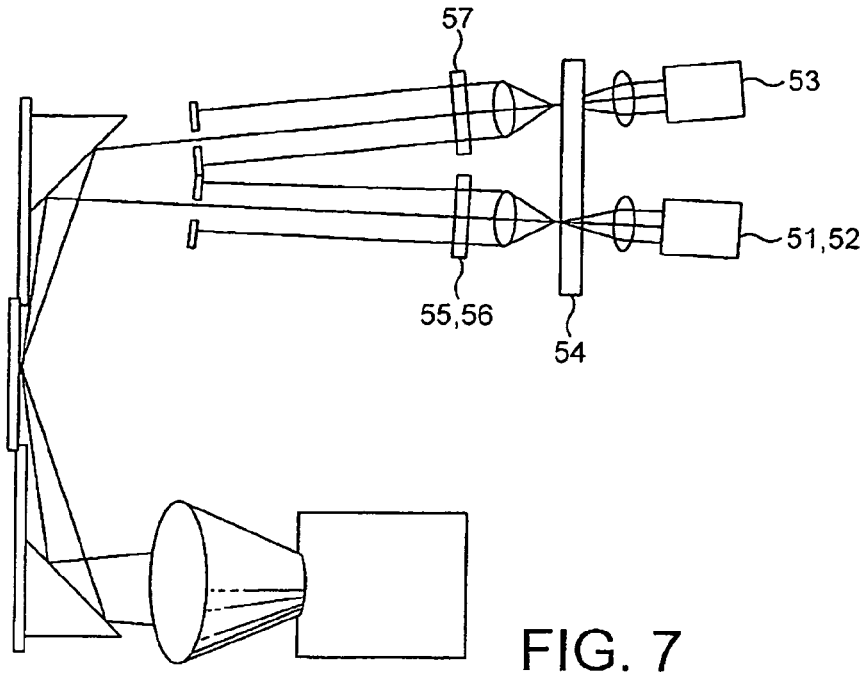
FIG. 7 shows a plan view of a sixth embodiment of the present invention.
Figure 8:
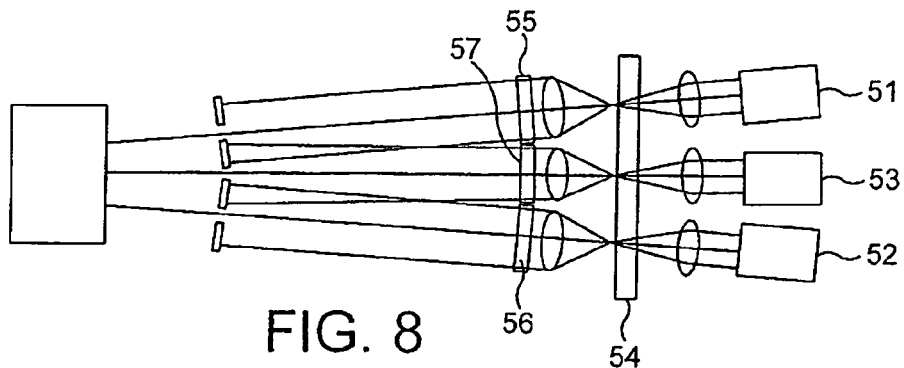
FIG. 8 shows a side view of the apparatus of FIG. 7.
Figure 9:
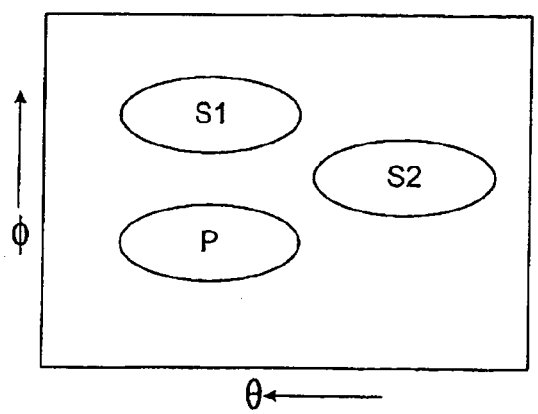
FIG. 9 shows a schematic diagram of the images detected using the apparatus of FIG. 7.

The use of three lasers, without polarisation switching, allows simultaneous imaging to be achieved. Such an arrangement is shown in FIGS. 7 and 8 which show a top view and side view respectively. The arrangement is an extension of the two-angle apparatus described in the first embodiment. Three lasers 51, 52 and 53 are arranged such that the beams of light produced pass through phase modulating beam expanders 54, before passing through respective fixed polarisers 55, 56, 57. Laser 51 is arranged so as to illuminate the sample at an angle of incidence θ=75° (measured in the plane of the paper in FIG. 7) and φ=+2° (measured in the plane of the paper in FIG. 8), and is S-polarised. Laser 52 is arranged to illuminate the sample at an angle of incidence θ=75° and φ=−2°, and is P-polarised. Laser 53 is arranged to illuminate the sample at an angle of incidence θ=73° and φ=0°, and may be either S or P polarised. The lasers may all be switched on at the same time, producing three images at the detector, as shown in FIG. 9. The images may be used to determine the surface characteristics in the same manner as the first embodiment. Of course, the three incident beams actually illuminate slightly different facet populations, but it is assumed that the inhomogeneity or non-isotropy in the surface is not sufficient to cause significant error. Whilst lasers 51 and 52 produce light of the same wavelength, laser 53 may produce light of the same, or a different wavelength.

Figure 10:
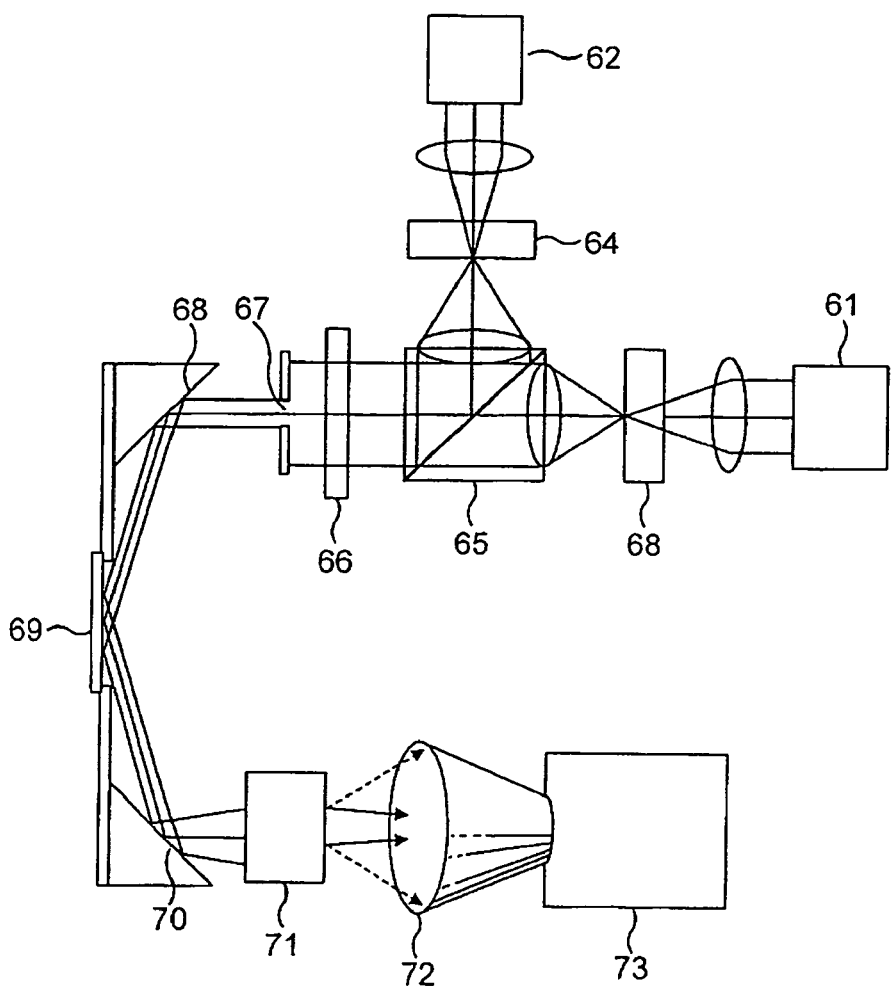
FIG. 10 shows a plan view of a seventh embodiment of the present invention.
Figure 11:
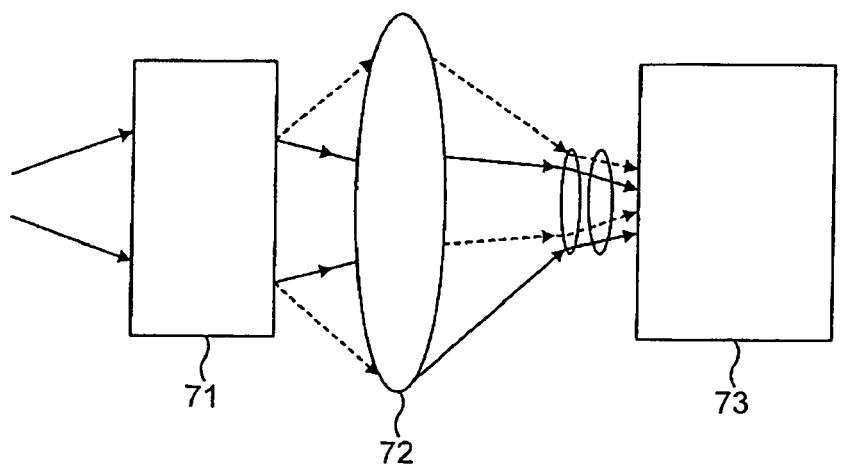
FIG. 11 shows a close-up view of the apparatus of FIG. 10.

A further embodiment of the invention is shown in FIGS. 10 and 11. A first laser 61 produces a collimated beam of light with wavelength 635 nm, whereas a second laser 62 produces a collimated beam of light with wavelength 690 nm, with an optical axis generally orthogonal to the first beam. The beams are passed through respective phase modulating beam expanders 63, 64 before entering a beam-splitter 65. The beam from laser 61 is transmitted through the beam-splitter and the beam from laser 62 is reflected by the beam-splitter so that they are coincident on leaving the beam-splitter. To remove any polarisation, the beams are passed through a depolariser 66. The depolarised beams pass through aperture 67, the diameter of which defines the area of the sample to be illuminated. The beams are guided onto the surface of the sample 69 at the same angle of incidence by plane mirror 68. The scattered beams are then guided by plane mirror 70 into a beam separating polariser 71. The beam separating polariser may be for example a Wollaston, Rochon or Senarmont prism. Light transmitted through the beam separating polariser is collected by lens assembly 72 into imaging detector 73.

The effect of the beam separating polariser 71 is shown in more detail in FIG. 11. The prism splits the scattered light into S and P polarised components, which leave the prism at different angles. The components are deviated by approximately 20°. The deviated components each form an image at the detector. The images may measured separately for each wavelength, and the surface characteristics determined as previously described. There may however be some overlap between the images formed by the components at the detector. In this case the S and P intensities may be extracted from the non-overlapped portions of the images and used to calculate the refractive index. The total integrated intensity from both images may be used to calculate gloss and micro-roughness. A modified algorithm may be used to calculate macro-roughness if the images overlap in the middle. The most practical way to determine micro-roughness is to use the two-wavelength approach, as described previously.

Figure 12:
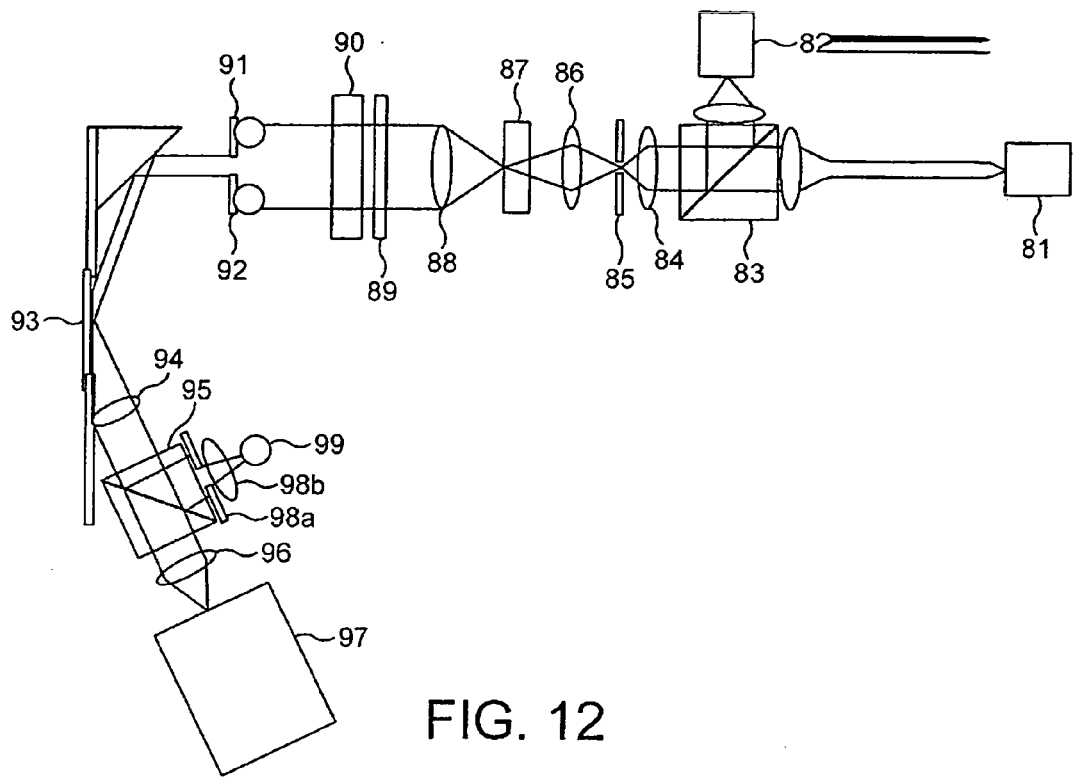
FIG. 12 shows a plan view of an eighth embodiment of the present invention.

FIG. 12 shows an eighth embodiment of the present invention, which is of a generally similar form to that shown in FIG. 5. Here, a first laser 81 may produce light of a first wavelength, for example 635 nm or 645 nm, while a second laser 82 may produce light of a second wavelength, for example 670 nm or 690 nm. The lasers are arranged so that they produce orthogonal collimated beams which pass through a beam splitter 83 to produce a coincident parallel beam. This beam is focused by a lens 84 onto an aperture 85 which acts as a spatial filter. The lens 84 and aperture 85 are not essential here but contribute to the system alignment stability. A lens 86 focusses the laser light onto a spinning diffuser 87 which demodulates the phase of the laser beam. Lens 88 then produces a collimated and expanded beam from the illuminated spot on the spinning diffuser, together diffuser 87 and lens 88 forming a "phase-modulating beam expander". The collimated and expanded beam then passes through a fixed polariser 89 which produces plane polarised light either parallel to or perpendicular to the surface of the specimen 93. A liquid crystal retarder 90 is used to switch the plane of polarisation between the states of parallel and perpendicular to the specimen surface. In this embodiment, a portion of the expanded polarised collimated beam falls onto photodiodes 91. These photodiodes are used to monitor the incident intensity of the beam. A remaining portion of the beam passes through aperture 92 which limits the width of the beam illuminating the surface. As in previous embodiments, a mirror reflects the collimated light onto the surface of the specimen 93 at a fixed angle of incidence, here nominally 75°. Light forward scattered from the surface of the specimen 93 within an angular range of approximately ±10° is collected by a lens 94 and passes through a non-polarising beam splitter 95.

Approximately 50% of the light intensity is passed through a second lens 96 and focussed onto imaging detector 97. The optics are chosen such that position on the imaging device corresponds to the angle at which the light is scattered from the surface. Approximately 50% of the light entering the non-polarising beam splitter 95 is reflected through an aperture 98a and lens 98b and is collected by a photodiode 99. The exact fraction of light directed by the beam splitter onto the imaging device and onto the photodiode 99 is determined by calibration. The aperture 98a approximately defines the angular range over which the photodiode collects light.

As in the embodiment of FIG. 5, at least three sets of images and intensity data are taken using the imaging detector using polarised light of two different wavelengths and two orthogonal polarisation directions, e.g. a first image at the first wavelength and first polarisation, a second image at the first wavelength and second polarisation and a third image at the second wavelength and first or second polarisation.

The macroroughness is obtained from the standard deviation of the angular distribution of the forward scattered light as measured on the imaging detector 97. The refractive index and microroughness may then be calculated using the intensity of the scattered light as described previously. A potential problem with the imaging detector for measuring specularly reflecting samples is that a very small intense spot may be formed on the image which gives poor measurement statistics. The photodiode 99 is not limited in this respect and is therefore appropriate for measuring the intensity for specularly reflecting samples. With proper calibration, the 5 photometric measurements may be made using both imaging and photodiode detectors.

Before use the reflectometer is calibrated using a highly polished glass of known refractive index. Measuring this sample gives the intensities in the various measurements states corresponding to known refractive index and zero microroughness. This calibration eliminates the need to know precisely the reflection and transmission characteristics of the various optical components in the system.

Figure 13:
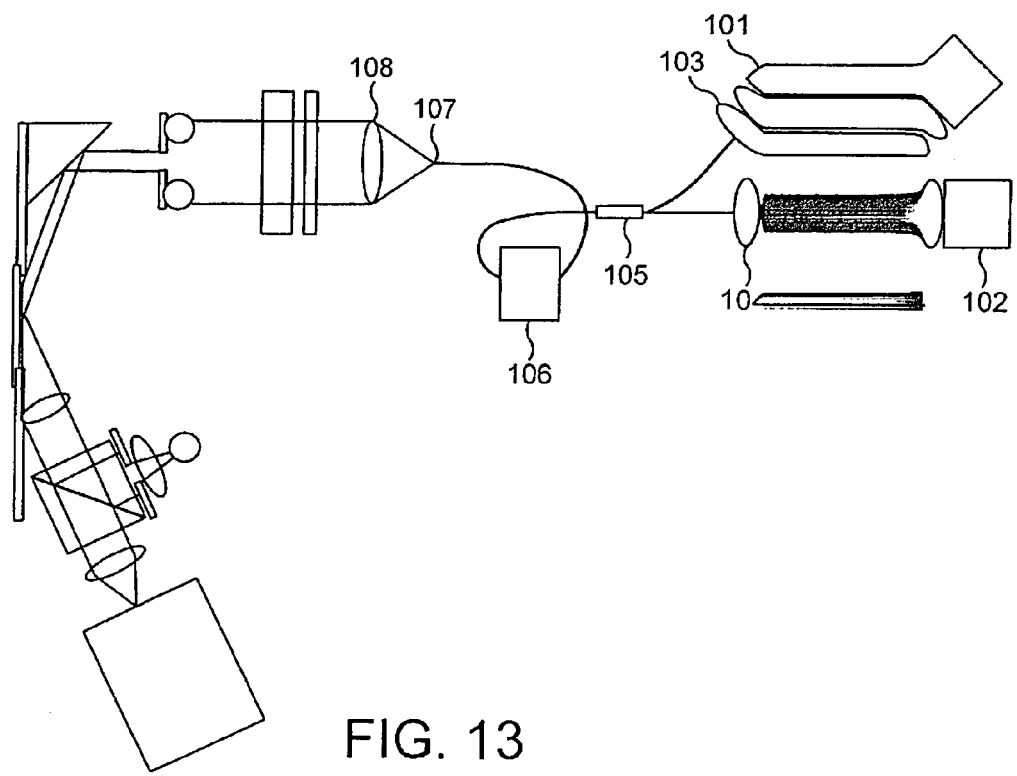
FIG. 13 shows a plan view of a ninth embodiment of the present invention.

FIG. 13 shows a further embodiment of the present invention, which is shown as including similar photodiode measurement components as in FIG. 12. Here though, the polarising beam splitter and phase-modulating beam expander components are replaceable by a fibre optic system. Two lasers, 101, 102 of different wavelengths, e.g. 635 or 645 nm and 670 or 690 nm are coupled by lens systems 103, 104 respectively into a bifurcated optical fibre 105. The optical fibre may simply be used to replace the polarising beamsplitter, lens and aperture of the previous embodiment in which case the end of the combined fibre 107 effectively becomes the aperture. The exit diameter of the fibre may be approximately 100 μm. However, preferably the optical fibre is also used to replace the spinning diffuser for phase modulation of the laser beam. Bending the optical fibre effectively changes its length and this in turn changes the phase of the laser light being emitted. By flexing the fibre very rapidly, the phase of the laser light emitted can be varied during the time taken to acquire intensity or image data. In FIG. 13 this flexing is achieved using a piezo-electric device or electromagnetic switch 106. This procedure averages the phase and reduces unwanted speckle effects. The end of the optical fibre 107 acts as a common aperture for both laser light sources. Light diverging from the end of the optical fibre is collected by a lens 108 and collimated. The remainder of the apparatus, as well as its operation is the same as for the previous embodiment.

Figure 14:
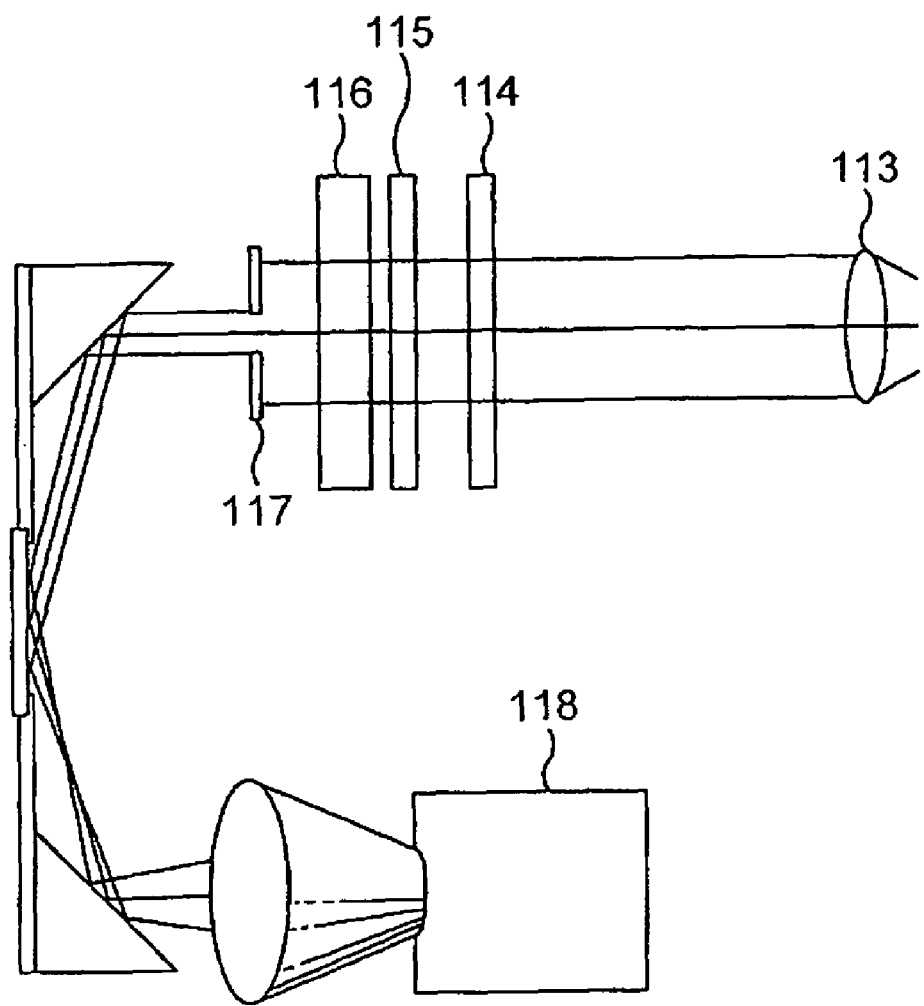
FIG. 14 shows a plan view of an tenth embodiment of the present invention.

FIG. 14 shows a further embodiment of the invention, which makes use of a polychromatic source. In recent years, many industries, notably the paint printing, automotive, plastics and cosmetics industries have greatly increased interest in special effects pigments. These pigments confer distinctive optical properties which cause an object to change appearance as a function of angle of view or angle of illumination. Examples of such pigments include metallic flakes or high aspect ratio pearlescent mineral particles. A parameter of interest for such systems is the colour shift with angle about the specular angle. Also of importance for these systems is the orientation distribution of the platey or flaky pigment particles which may be described by the facet model, or a derivative of it—the flake model, which basically describes facets covered by a transparent film, for example the resin in a paint system. In the embodiment shown, a high intensity polychromatic light source 111, for example a halogen bulb or white light LED, illuminates a pinhole 112 with a nominal diameter of around 100 μm. A reflector (not shown) may be used to focus light onto the pinhole to maximise intensity. Light is collimated by a lens 113 and passed through a broadband filter 114 to define the range of wavelengths and exclude undesirable wavelengths in the IR if present. The light is then plane polarised, either parallel or perpendicular to the plane of the sample surface by sheet polariser 115, and passed through a liquid crystal retarder 116, which is used to selectively rotate the plane of polarisation between the states of parallel and perpendicular to the sample surface plane. The area of sample illuminated is defined by passing the polarised light through aperture 117. The light is guided onto the sample and the scattered light collected and passed through a lens assembly as in the other embodiments previously described. The imaging detector 118 used is a colour imaging device, e.g. a colour camera.

With this embodiment, the sample is illuminated with P-polarised polychromatic light and an image is obtained which is separated into red, green and blue (RGB) intensities by the colour imaging device 118. The colour imaging device 118 uses filters to separate the colour components of the beam, and the R, G and B are hence wavebands determined by the camera characteristics. The polarisation is rotated to give S polarised light with respect to the surface and a second RGB image obtained. A refractive index is calculated for each colour (wavelength average) from the S and P intensities using procedures described for previous embodiments.

The relative intensities of the incident S and P light in each colour waveband is previously determined by measuring the reflection of a highly glossy material of known refractive index and dispersion. This calibration measurement also allows the relative intensity of R, G and B light in the incident beam to be determined, and the total intensity in each colour band to be determined.

The micro-roughness is obtained by comparing the intensity of colour pairs R-B, G-B and G-R for a given polarisation and using the method for determination by two wavelengths (described with reference to FIG. 5).

In the calculation of refractive index and micro-roughness, intensities are used which are averaged over a wavelength interval defined by the colour discrimination characteristics of the imaging device. Both refractive index and micro-roughness vary with wavelength. In the absence of high absorption, changes to refractive index may not be large, and the refractive index obtained for a given colour interval is an average defined by the transmission characteristic of the filter used in the imaging device for the given colour, i.e. determined by the average reflectance over the given wavelength interval. Similarly micro-roughness will be an average based upon wavelength averaged reflectance values.

The macro-roughness is determined directly from the image of reflected light on the detector for each of R, G and B and at the two polarisation states.

A value for the gloss at each of the colours R, G and B is determined as described with reference to previous embodiments.

The colour shift relative to the colour at the specular angle is determined as a function of angle about the specular angle. RGB colour as measured may be converted to other colour representations; for example CIE L*a*b* according to well-known procedures. This parameter is of interest for special effects pigments.

In each embodiment described, a supplementary converging lens may be inserted with its front focal point at or near to the centre of the illuminated area on the sample. This lens produces an image of the sample surface, and in the case of specularly reflecting materials, effectively spreads the reflected beam over a larger area on the imaging detector. The low-angle image of the surface can be useful in some circumstances, presenting an impression of the spatial distribution of roughness features. For specularly reflecting samples, it is advantageous to spread the reflected beam over a large number of pixels on the imaging detector to obtain better intensity statistics. Other possibilities for achieving a spread of the reflected beam will be obvious to those skilled in the optical arts, including for example inserting a diverging lens immediately before the imaging lens assembly, or modifying that assembly directly.

In all embodiments, before measurements are made it is necessary to calibrate the system in some way to define the various incident intensities. This calibration is readily done using a highly polished glass plate of known refractive index. During operation of the instrument it may be desirable to continue to monitor the absolute and relative intensities of the various light sources, in a position after the phase modulating beam expander, but before the sample. By measuring the incident intensities in this way, it is possible to correct calibrated intensities according to any variations in light source output over a period of time. Ways of monitoring incident light will be apparent to those skilled in the art. For example, in FIG. 5, a photodiode could be mounted on the unused port of the beam-splitter 29.

Although the invention has been described with reference to the embodiments above, there are many other modifications and alternatives possible within the scope of the claims. It is envisaged that the invention will be of particular application in the paper industry, to determine paper surface characteristics, although the invention is not limited to this field. It is not necessary to use lasers for the sample illumination, any collimated light source of suitable intensity could be used, for example filtered LEDs. In this case it would be unnecessary to use a phase modulating beam expander, as the light from an LED is substantially incoherent. Any type of switchable polariser could be used in place of the liquid crystal retarder. The surface characteristics may be mapped to the surface by repeating the measurements at a variety of points on the surface, and there may be adjustable mounting means for the sample to enable this to be done with the minimum of disruption to the apparatus. The wavelengths and angles of incidence quoted are exemplary only, and any suitable values may be selected for these depending on application and equipment available etc. The phase modulating beam expander used may comprise any suitable apparatus, for example a reflection diffuser may be used.

The invention claimed is:

1. A method for determining a surface characteristic of a sample, comprising the steps of:
   a) illuminating a surface of the sample with first and second collimated beams of light; and;
   b) using an imaging detector to record an intensity angular distribution image of the light from beams reflected from the surface,
      wherein said first and second collimated beams are selected from the group consisting of:
      beams having different incidence angles, beams having different polarization, and beams having different wavelengths.

2. A method according to claim 1, wherein first, second and third beams of light are used to illuminate the surface, the imaging detector recording an intensity distribution image of each reflected beam.

3. A method according to claim 2, wherein the first and third beams are plane polarized and the second beam is polarized at 90° to the first and third beams.

4. A method according to claim 3, wherein the first and third beams are plane polarized either perpendicular or parallel with respect to the surface of the sample.

5. A method according to claim 4, wherein the first and second beams have the same wavelength, and illuminate the surface at the same angle of incidence.

6. A method according to claim 5, wherein the third beam has a different wavelength from the first and second beams.

7. A method according to claim 6, wherein the third beam illuminates the surface at the same angle of incidence as the first and second beams.

8. A method according to claim 5, wherein the first, second and third beams have the same wavelength.

9. A method according to claim 8, wherein the third beam illuminates the surface at a different angle of incidence from the first and second beams.

10. A method according to claim 2, wherein the first, second and third beams illuminate the surface sequentially.

11. A method according to claim 2, wherein the first, second and third beams illuminate the surface simultaneously.

12. A method according to claim 1, wherein the reflected light is split into two orthogonally polarized components before reaching the imaging detector.

13. A method according to claim 12, wherein the light is split by passing it through a beam separating polarizer.

14. A method according to claim 1, wherein said method is used to determine a plurality of surface characteristics of the sample.

15. A method according to claim 14, wherein one of said surface characteristics determined is selected from the group consisting of: the surface refractive index of the sample, the gloss of the surface of the sample, the macro-roughness of the surface of the sample, the micro-roughness of the surface of the sample, and the angular colour shift.

16. A method according to claim 15, further comprising the step of determining the surface refractive index of the sample, the gloss of the surface of the sample, the macro-roughness of the surface of the sample and the micro-roughness of the surface of the sample.

17. A method according to claim 1, further comprising the step of determining the refractive index of the sample by comparing a measured reflected intensity of a plane polarized reflected beam with a measured reflected intensity of an orthogonally polarized reflected beam.

18. A method according to claim 1, further comprising the step of determining the gloss of the surface of the sample from the integrated reflectance measured by the imaging detector.

19. A method according to claim 1, further comprising the step of determining the macro-roughness of the surface of the sample by using a facet angle model to produce a facet angle distribution of the surface and measuring the width of the intensity distribution.

20. A method according to claim 1, further comprising the step of determining the micro-roughness of the surface of the sample by calculating the ratio of the intensity in the images produced by two beams of the same polarization but with different angles of incidence on the surface.

21. A method according to claim 1, further comprising the step of determining the micro-roughness of the surface of the sample by calculating the ratio of the intensity in the images produced by two beams of the same polarization but with different wavelengths.

22. A method according to claim 1, further comprising the step of determining the micro-roughness of the surface of the sample by:
   a) measuring the total reflectance in Aobs of images produced by a beam of a first polarization;
   b) calculating the total reflectance in Acalc for a surface with the same refractive index as the sample but with negligible micro-roughness; and
   c) comparing Aobs with Acalc to determine a micro-roughness.

23. A method according to claim 1, further comprising the step of determining the micro-roughness of the surface of the sample by:
   a) measuring the total reflectance in Aobs of images produced by a beam of a first polarization and a beam of orthogonal polarization;
   b) calculating the total reflectance in Acalc for a surface with the same refractive index as the sample but with negligible micro-roughness;
   c) comparing Aobs with Acalc for both polarizations to determine a micro-roughness associated with each polarization; and
   d) averaging the micro-roughnesses associated with each polarization to derive the micro-roughness of the surface.

24. A method according to claim 1, further comprising the step of determining the color shift relative to the color at the specular angle.

25. A method according to claim 1, further comprising the steps of determining surface characteristics at a plurality of positions on the sample.

26. A method according to claim 1, wherein the light beams are produced by a incoherent source.

27. A method according to claim 26, wherein the light source is a LED.

28. A method according to claim 26, wherein the light source is polychromatic.

29. A method according to claim 1, wherein the light beams are produced by a coherent source, and are phase modulated before they illuminate the sample.

30. A method according to claim 29, wherein the light source is a laser.

31. A method according to claim 29, wherein the phase modulation is produced by a first lens, a spinning diffuser and a second lens, a surface of the spinning diffuser being positioned at the focal point of both of said first and second lenses.

32. A method according to claim 29, wherein the phase modulation is produced by passing the light beams through an optical fiber, the optical fiber being flexed in use so as to modulate the phase of the light beams.

33. A method according to claim 1, wherein the intensity of the reflected beam is measured using a photodiode.

* * * * *